United States Patent [19]

Whitney et al.

[11] 4,269,185
[45] May 26, 1981

[54] SELF CONTAINED MECHANICAL INJECTOR

[76] Inventors: Douglass G. Whitney, 2518 W. Wesley Rd.; John K. Martin, III, 2837 Ridge Wood Cir., both of, Atlanta, Ga. 30327

[21] Appl. No.: 25,047

[22] Filed: Mar. 29, 1979

Related U.S. Application Data

[60] Continuation-in-part of Ser. No. 1,091, Jan. 8, 1979, which is a division of Ser. No. 741,528, Nov. 12, 1976, Pat. No. 4,150,672, and a continuation-in-part of Ser. No. 741,528, Nov. 12, 1976, Pat. No. 4,150,672, and a continuation-in-part of Ser. No. 964,953, Nov. 30, 1978.

[51] Int. Cl.³ .................. A61M 5/00; A61M 5/20
[52] U.S. Cl. .................. 128/214 F; 128/DIG. 1; 128/218 A
[58] Field of Search ......... 128/214 F, 218 A, DIG. 1, 128/DIG. 12, 234, 235, 273

[56] References Cited

U.S. PATENT DOCUMENTS

| | | | |
|---|---|---|---|
| 2,602,446 | 7/1952 | Glass et al. | 128/218 A |
| 2,627,270 | 2/1953 | Glass et al. | 128/218 A |
| 2,690,178 | 9/1954 | Bickford | 128/213 R |
| 2,702,547 | 2/1955 | Glass et al. | 128/218 A |
| 2,703,084 | 3/1955 | Tomlinson | 128/214 F |
| 3,279,653 | 10/1966 | Pfleger | 128/218 A |
| 4,059,110 | 11/1977 | Wuthrich | 128/218 A |
| 4,150,672 | 4/1979 | Whitney et al. | 128/214 F |

*Primary Examiner*—Dalton L. Truluck
*Attorney, Agent, or Firm*—B. J. Powell

[57] ABSTRACT

Apparatus and method for injecting fluids into patients at a controlled rate from an ampule containing the injecting fluid with a sliding piston therein to force the fluid from the ampule into the patient using a drive system which incrementally and successively advances the piston in the ampule to meter the fluid into the patient.

12 Claims, 4 Drawing Figures

SELF CONTAINED MECHANICAL INJECTOR

CROSS-REFERENCE TO RELATED APPLICATIONS

This application is a continuation-in-part of our co-pending application Ser. No. 001,091, filed Jan. 8, 1979, which is a division of our co-pending application Ser. No. 741,528, filed Nov. 12, 1976; and a continuation-in-part of our co-pending application Ser. No. 741,528, filed Nov. 12, 1976, now U.S. Pat. No. 4,150,672 and Ser. No. 964,953, filed Nov. 30, 1978.

I. TECHNICAL FIELD

This invention relates generally to devices for dispensing or injecting a fluid at a controlled rate and more particularly to an injector for use in the medical field to inject fluids into the body of a patient at a slow rate over a prolonged period of time.

II. BACKGROUND ART

It is desirable in the medical profession to inject fluids such as liquid medicaments into the body of the patient, whether human or animal, at a relatively slow rate over a prolonged period of time. Several varieties of medical treatments such as chemotherapy, pre- and post-surgery treatments for the prevention of blood clotting, various nutrient treatments, various antibiotic treatments and treatment of certain other diseases generally required low rates of injection over a long period of time. Such injections are generally made intravenously or subcutaneously into the patient. Some of these treatments generally require that the fluid be introduced relatively continuously over an extended period of time at varying rates ranging from very slow rates, usually about 1 cc per 24-hour period, to relatively fast rates of more than about 5 cc per 24-hour period. Because a significant increase in the predetermined rate of injection during these continuous treatments must be accurately controlled to prevent serious injury to or fatality of the patient, the rate of injection must be frequently and closely monitored.

There are a number of liquid dispensing or injection devices presently known which attempt to dispense or inject a liquid into a patient at a very slow continuous rate over an extended period of time. These prior art injection systems, however, suffer from a number of drawbacks.

One problem frequently encountered with such prior art injection systems is that the system cannot reliably inject small quantities of fluid over a prolonged period of time. To compensate for this inadequacy, medical personnel have had to dilute the liquid medicament with neutral fluids to reduce the unit liquid medicament concentration of the fluid being injected so that a relatively large quantity of fluid could be injected without overdosing the patient with the active liquid medicament and so that the undesired consequences due to variations in fluid injection rate were minimized. This, of course, increases the weight of the fluid being injected and also increases the power required to inject this larger quantity of fluid into the patient. The net result is that the overall weight of these systems due to the weight of the fluid to be injected and the weight of the necessary power supply is at a level that virtually precluded these injection systems being made sufficiently portable for the patient to carry on his usual daily activities.

Another problem commonly found with the prior art injection systems is that a failure in some component of the system can cause the injection system to exceed the desired injection rate. This not only has resulted in the use of the diluted liquid medicament but has also required frequent monitoring of the injection system by medical personnel to compensate for this problem. To further compensate for this problem, the patient has usually been confined to a medical facility so that counteractive treatment is quickly available in the event of over-dosage of the patient.

III. SUMMARY OF THE INVENTION

According to the invention, there is provided a method of and apparatus for injecting fluid into a patient at an average prescribed injection rate over a prolonged period of time from a chamber carrying the fluid with an outlet connecting the fluid to the patient and with a piston in the chamber movable toward the outlet to force the fluid into the patient characterized by the steps of connecting the piston to a mechanical, spring driven, driving means constructed and arranged to move the piston only a prescribed distance toward the outlet each time the driving means is operated to force a known volume of the fluid into the patient each time the piston is moved the prescribed distance at an injection rate greater than the desired average prescribed rate where the known volume is much less than the total volume of fluid to be injected over the prolonged period of time; and alternatively operating and stopping the operation of the driving means to cause the fluid to be injected at the average prescribed rate over the sum of the times the driving means is operated and not operated.

In summary, the invention of this application overcomes the problems and disadvantages associated with the prior art by providing an injection system which has the capability of injecting fluid slowly and precisely into a patient at a known, easily measurable and easily variable rate. Because the system of the invention is able to precisely control the injection of the fluid, the volume and thus the weight of the fluid injected is minimized because of its concentrated form rather than diluted form. Also, the power required to dispense this minimized volume of fluid is minimized to minimize the power back weight. As a result, the system of the invention can be made highly portable so that the patient is not hampered in his ambulatory capability thereby maximizing the amount of productive time available to the patient even during treatment. Because of these features, the system of the invention is ideally suited for out-patient use not presently clinically available to prevent unnecessary hospitalization and expense.

These and other features and advantages of the invention disclosed herein become more apparent upon consideration of the following detailed description and accompanying drawings wherein like characters of reference designate corresponding parts throughout the several views and in which:

Figure 1:
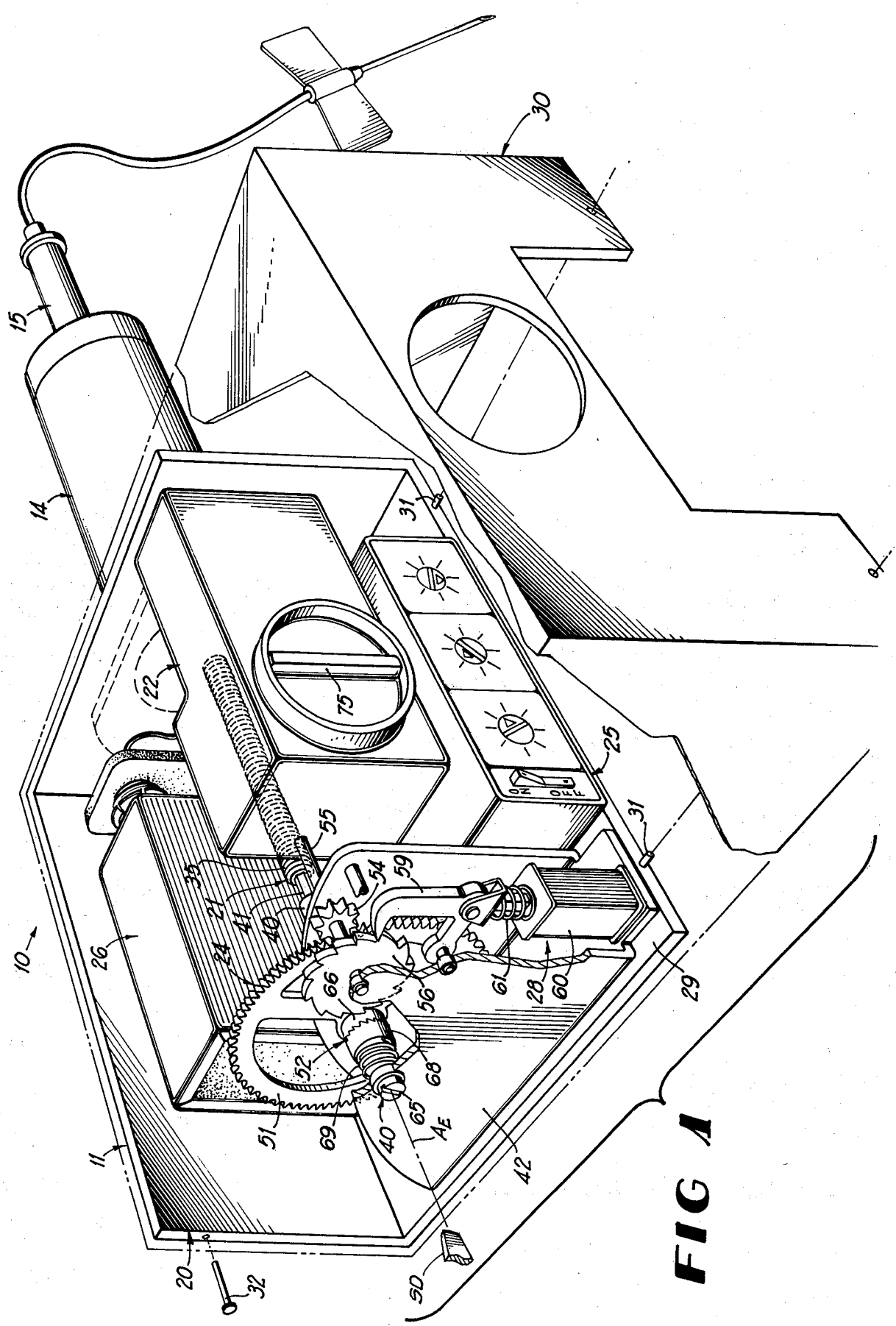
FIG. 1 is an exploded perspective view illustrating the apparatus with portions thereof broken away to show the construction thereof.

These figures and the following detailed description disclose specific embodiments of the invention; however, it is to be understood that the inventive concept is not limited thereto since it may be embodied in other forms.

DETAILED DESCRIPTION OF ILLUSTRATIVE EMBODIMENTS

Referring to the figures, it will be seen that the fluid injector 10 has a power unit 11 for selectively forcing a fluid from the ampule or container 12 carrying the fluid. The ampule 12 is positioned on the power unit 11 by an ampule holder 14. Thus, the fluid from the ampule 12 is forced into the patient by the power unit 11 via a connector assembly 15.

The power unit 11 includes a housing 20 which removably mounts the ampule holder 14 thereon about an expelling axis $A_E$ as will become more apparent. The housing 20 mounts a drive screw assembly 21 therein about the expelling axis $A_E$ to expel fluid from the ampule 12 carried in holder 14 as will become more apparent. The drive screw assembly 21 is driven by a spring driven clockwork mechamism 22 through a transmission 24. The output of the clockwork mechanism 22 is controlled by a controller 25 powered by a battery 26 to operate a solenoid clutch assembly 28 connected to the output of the clockwork mechanism 22 as will become more apparent.

The housing 20 has a base 29 which mounts the various components thereon. A removably cover 30 is adapted to fit over base 29 to enclose the components mounted on the base. Locating pins 31 maintain cover 30 in alignment with base 29 and latch pin 32 keeps cover 30 in place.

The drive screw assembly 21 includes an externally threaded drive screw 35 (FIGS. 1 and 2) which forces the fluid from ampule 12. The drive screw 35 is positioned coaxially along the expelling axis $A_E$ by an internally threaded split nut 36 (FIG. 2) mounted on the base 29 of housing 20 so that nut 36 is axially fixed along axis $A_E$. Nut 36 can be opened to release the drive screw 40 so that it can be manually moved axially along axis $A_E$ and nut 36 re-engaged. With nut 36 closed to engage drive screw 35, rotation of drive screw 35 shifts drive screw 40 axially along the expelling axis $A_E$ to engage the piston 38 in the ampule 12 and expel the liquid medicament from the ampule.

The drive screw 35 is driven from the drive shaft 40 through a slip joint 41 so that the drive screw 35 is axially shiftable along drive shaft 40, yet the drive shaft 40 maintains driving engagement with screw 35. Thus, drive screw 35 is rotated by drive shaft 40, yet is axially movable there along so that driving engagement is maintained while nut 36 extends drive screw 35.

Figure 2:
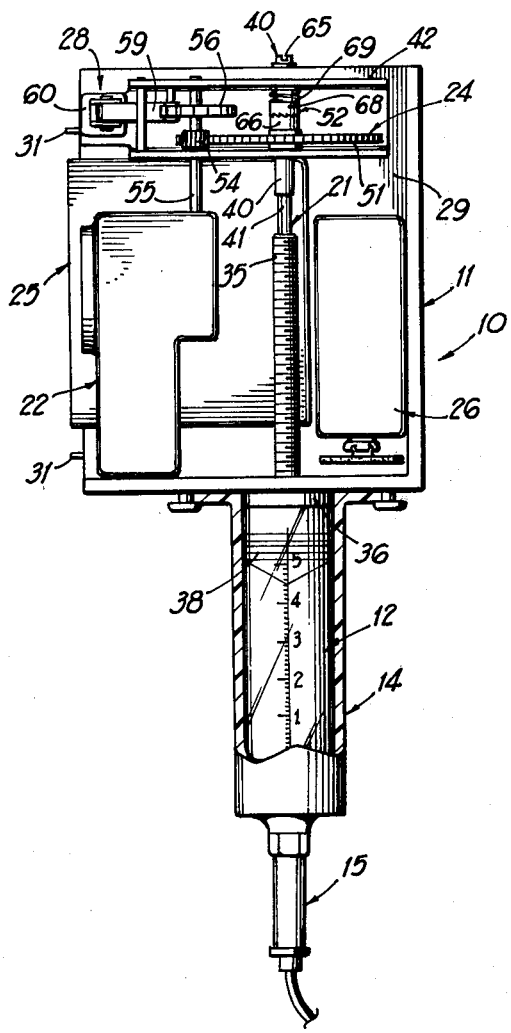
FIG. 2 is an elevational view partly shown in cross-section of that embodiment of the apparatus seen in FIG. 1.

The drive shaft 40 is rotatably journalled in bearings mounted in support plates 42 of the transmission 24 as seen in FIG. 1 so that the central axis of the drive shaft 40 is coaxial with the expelling axis $A_E$. The journalled connections between the drive shaft 40 and the support plates 42 prevent axial movement of the drive shaft 40 along the expelling axis $A_E$ while allowing the drive shaft 40 to be rotated about the expelling axis $A_E$. Thus, it will be seen that, as the drive shaft 40 is rotated clockwise as seen in FIG. 1 with the nut 36 closed about the drive screw 35, the drive screw 35 will be rotated to axially displace the drive screw 35 along the expelling axis $A_E$ and move the projecting end thereof out of the housing 20.

To retract the drive screw 35 back into the housing 20, the split nut 36 is opened and the drive screw 35 manually pushed back into the housing 20. After the drive screw 35 has been retreacted back into the housing 20, the split nut 36 is reclosed to re-engage the drive screw 35 so that it can be driven back out of the housing 20 by rotating the drive shaft 40.

The transmission 24 (FIGS. 1 and 2) is powered by the clock mechanism 22 to rotate the drive shaft 40. The drive shaft 40 serves as the output of the transmission 24 with an output spur gear 51 rotatably mounted on the drive shaft 40 between the support plates 42 and connected to the drive shaft 40 through a one-way ratchet clutch assembly 52 so that rotation of the output spur gear 51 rotates the drive shft 40. The output spur gear 51 is rotatably driven by an input drive pinion 54 driven by the clockwork mechanism 22. The input drive pinion 54 is mounted on the output shaft 55 of the clockwork mechanism 22 as will become more apparent.

The solenoid clutch assembly 28 is also mounted on the output shaft 55 between the transmission support plates 42. The clutch assembly 28 includes a ratchet wheel 56 affixed to the pinion shaft 55 and provided with peripheral ratchet teeth 58 which are engaged by a stop dog 59 best seen in FIG. 1. The ratchet teeth 58 on the ratchet wheel 56 are oriented with respect to the stop dog 59 so that the ratchet wheel 56 can rotate with the output shaft 55 in a counterclockwise direction as seen in FIG. 1 when the stop dog 59 is pivoted outwardly to its released position by solenoid 60 when it is activated. The return spring 61 on the solenoid 60 resiliently urges the stop dog 59 toward its catch position. Thus, release of stop dog 59 by actuating solenoid 60 allows the clockwork mechanism 22 to rotate the drive pinion 54 counterclockwise until the dog 59 returns to its catch position by spring 61. Then stop dog 59 engages the next ratchet tooth 58 to stop the motion of pinion 54 and thus limit the amount of fluid injected from ampule 14.

A flush mechanism is provided by extending the projecting end of the drive shaft 40 through the outboard support plate 42 and providing a slot 65 in the projecting end of drive shaft 40 to be engaged by a driving device SD such as a screwdriver to manually rotate shaft 40 clockwise. The input ratchet assembly 52 serves to connect gear 51 to drive shaft 40 so that rotation of shaft 40 clockwise, when viewed as seen in FIG. 1, will allow gear 51 to remain stationary for flushing, yet rotation of gear 51 clockwise also rotates shaft 40 clockwise as will become more apparent.

Ratchet assembly 52 includes driving ratchet member 66 affixed to the spur gear 51 so that it rotates therewith. An internally splined driven ratchet member 68 is mounted on the drive shaft 40 between support plates 42 via an externally splined connector affixed to shaft 40. The splined connector permits driven ratchet member 68 to slide axially along shaft 40 but rotation of driven ratchet member 68 positively rotates the drive shaft 40. The ends of ratchet members 66 and 68 facing each other are forced together by ratchet spring 69 and are provided with meshing ratchet teeth constructed so that the driving ratchet member 66 rotates the driven ratchet member 68 when spur gear 51 is rotated clockwise viewed as in FIG. 1; however, the teeth on the driven ratchet member 68 can slip over the teeth on the driving ratchet member 66 when shaft 40 is rotated clockwise so that flushing is provided. This feature is more fully explained in our co-pending application Ser. No. 001,091 and incorporated herein by reference.

Figure 3:
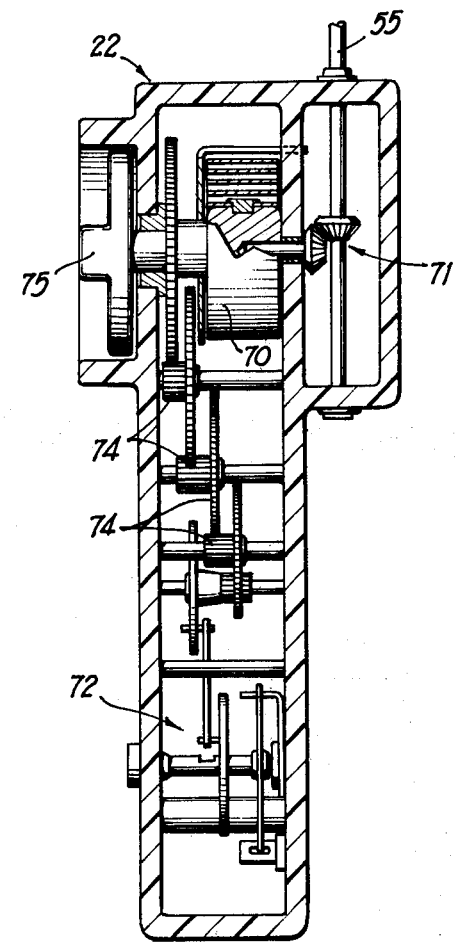
FIG. 3 is an enlarged view of the spring drive mechanism of the apparatus taken along line 3—3 in FIG. 1; and, FIG. 4 is an electrical block diagram of the controller circuit of the invention seen in FIGS. 1-3.

The clockwise mechanism 22 as best seen in FIG. 3 includes a mainspring 70 driving the output shaft 55 through a right angle gearing 71. The output rotational speed of the shaft 55 is controlled by a typical escapement mechanism 72 and associated gear train 74 of conventional design and, hence, a detailed explanation is not necessary. The mainspring 70 is manually wound with key 75.

The ampule 12, ampule holder 14, connector assembly 15, and drive screw assembly 21 have been described in detail in our co-pending application Ser. No. 001,091 and the description thereof is incorporated herein by reference. Therefore, a detailed description will not be repeated here. The connector assembly 15 has an injection needle 76 for intravenously or subcutaneously connecting the liquid medicament in the ampule 12 to the patient so that movement of the piston 38 by power unit 11 forces the liquid medicament into the patient.

Figure 4:
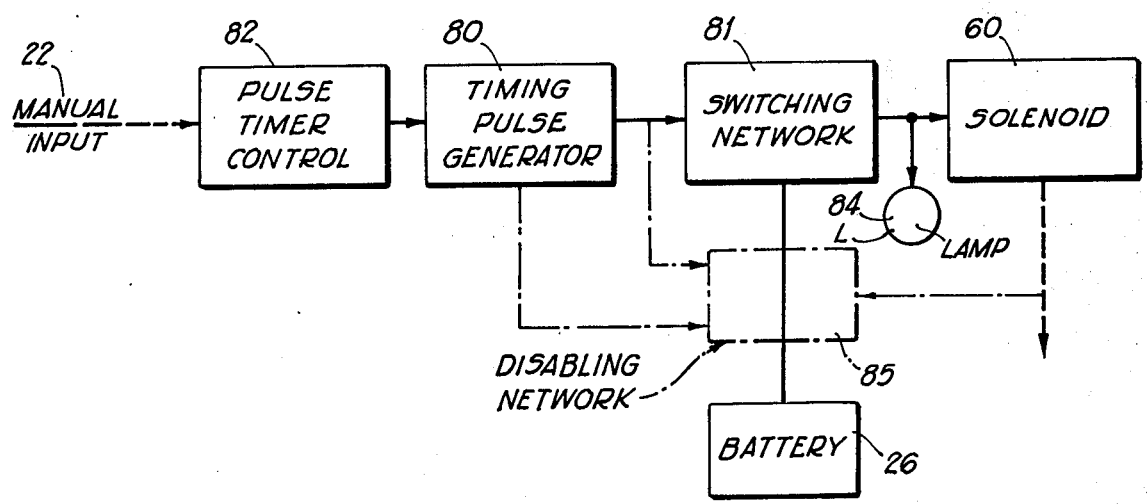

The controller 25 serves to alternatively connect and disconnect the battery 26 to solenoid 60 in clutch assembly 28 so that the stop dog 59 alternatively releases and stops the ratchet wheel 56. When the ratchet wheel 56 is released, the clockwork mechanism 22 drives the spur gear 51 and drive screw 35 to expel the liquid medicament. When the controller 25 disconnects battery 26 from solenoid 60, return spring 61 shifts stop dog 59 back to its catch position so that it engages the next ratchet tooth 58 on wheel 56 to stop the clockwork mechanism 22 from further driving the spur gear 51 and drive screw 35 until the controller 25 again connects the solenoids 60 to battery 26. The rate at which controller 25 connects and disconnects battery 26 to solenoid 60 thus serves to maintain the desired average liquid injection rate. The controller 25 is schematically illustrated in FIG. 4. Basically, the controller 25 includes a timing pulse generator 80 whose pulse output operates a switching network 81 to cause the switching network 81 to alternatively connect the solenoid 60 to and disconnect solenoid 60 from battery 26. The pulse output rate from the timing pulse generator 80 can be manually adjusted through the pulse time control 82. The pulse timer control 82 is illustrated in FIG. 1 as three manually adjustable potentiometers although different timer control arrangements may be used.

The operation of the timing pulse output of controller 25 is described in detail in our co-pending application Ser. No. 001,091 and is incorporated herein by reference. Basically, the duty cycle of the timing pulse generator 80 is such that the switching network 81 connects the battery 26 to the solenoid 60 for a first period of time and then disconnects it for a second period of time. Preferably, the connected "ON" period is maintained fixed while the disconnected "OFF" period is varied to vary the overall injection rate as more fully described in our co-pending application Ser. No. 001,091. In this application, the "ON" is usually selected to be less than the time it takes the clockwork mechanism 22 to move the ratchet wheel 56 the distance between adjacent teeth 58 so that the drive screw 35 is only advanced one ratchet tooth 58 at the time. If is, of course, within the scope of the invention to allow more than one tooth of movement of the ratchet wheel 56 during the "ON" period.

An indicator mechanism 84 such as lamp L seen in FIG. 4 or an audible sound generator may be used to provide an indication that the injector is operating. The indicator mechanism may be activated with the output from generator 80. Since the "ON" state is usually shorter than the "OFF" state, however, it would usually be activated in response to the "ON" state to extend battery life.

By appropriately selecting the components of controller 25, the gear ratios of the various mechanical components of power unit 11 and the size of ampule 12, the setting of the pulse time control 82 can be made to correspond to the injection rate delivered. For instance, with the three potentiometers illustrated in the control 82, the setting could correspond to the injection rate to two decimal places. This facilitates adjustment of injection rate.

It will be appreciated that the overall gear ratio of transmission 24 and the drive screw assembly 21 will be determined by the size of the ampule 12, the tooth spacing on ratchet wheel 56, and the desired incremental volume of liquid medicament to be injected each time the solenoid 60 is energized. Simply for ease of monitoring, one set of parameters used was one energized time each minute for solenoid 60 when an injection rate of about 1 cc per 24-hour period was selected. Thus, each time solenoid 60 is energized, about 0.0007 cc of liquid medicament is dispensed.

To protect against the controller 25 overdosing the patient through failure of one or more of the components, the battery 26 may be connected to the switching network 81 through a disabling monitor network 85 shown by phantom lines in FIG. 4. The disabling network 84 is provided with a feedback circuit from the timing pulse generator 80 and the output of the pulse generator 80 so that malfunction of the timing pulse generator 80 causes the feedback circuit to activate the disabling monitor network 84 to cause the disabling monitor network 84 to disconnect the battery 26 from the switching network 81 and thus disable the solenoid 60. A motion sensor may be operatively associated with the mechanical output of the solenoid 60 and/or the clockwork drive to provide another input to the disabling monitor network 84 so that, if the timing pulse generator 80 generates a signal in its output which should cause the switching network 81 to activate the solenoid 60 and no motion is sensed in the mechanical output of the solenoid 60 or clockwork drive, the disabling monitor network 84 disconnects the battery 26 from the switching network 81 to disable the solenoid 60. Thus, the disabling monitor network 84 serves to disable the solenoid 60 upon malfunction of the timing pulse generator or the failure to obtain a mechanical output from the solenoid 60 or clockwork drive when such output should be present.

We claim:

1. Apparatus for selectively dispensing a fluid at a controlled slow rate into a patient comprising:
   container means defining a fluid chamber therein for containing the fluid to be dispensed and defining a fluid outlet therefrom through which the fluid is to be dispensed into the patient;

expelling means operatively associated with the fluid in said container means to expel the liquid from said container means, said expelling means including a piston member slidably mounted in said fluid chamber for positively forcing the fluid from said fluid chamber as said piston member moves toward the outlet end of said fluid chamber, said piston member moved toward the outlet end when said expelling means is driven;

spring operated driving means for selectively driving said expelling means to force said piston member toward the outlet end of said fluid chamber; and control means operatively connected to said driving means for selectively and successively causing said driving means to move said piston member to successively and incrementally force the fluid from said fluid chamber in said container means into the patient at a selected prescribed average rate over a prolonged period of time, said control means alternatively releasing said driving means for a first prescribed short period of time fo fixed duration so that said driving means causes said expelling means to force fluid from said fluid chamber in said container means at a first prescribed rate greater than the selected prescribed average rate and said control means alternatively arresting the operation of said driving means for a second prescribed short period of time to stop the fluid flow from said fluid chamber so that the fluid is forced from said fluid chamber in said container at the selected prescribed average rate over the sum of said first and second periods of time, said control means including adjustment means for selectively varying the duration of only said second prescribed short period of time without varying the duration of said first prescribed period of time to selectively vary the selected prescribed average rate at which the fluid is forced from said fluid chamber of said container into the patient.

2. The apparatus of claim 1 wherein said control means includes stop clutch means for physically limiting the amount of movement transmitted from said driving means to said piston each time said driving means is released for operation.

3. The apparatus of claim 2 further including manually operated flushing means operatively connected to said piston for selectively moving said piston independently of said driving means.

4. The apparatus of claim 2 wherein said stop clutch means further includes mechanical ratchet means operatively connected to said driving means to selectively arrest the operation of said driving means and electrically operated controller means for selectively controlling the operation of said mechanical ratchet means.

5. The apparatus of claim 4 wherein said controller means includes an electrical power supply, timing pulse generator means and switching means operated by said timing pulse generator means; and wherein said ratchet means includes solenoid means for selectively causing said ratchet means to release said driving means for operation when said solenoid means is electrically actuated and to arrest the operation of said driving means when electrically de-actuated, said switching means selectively connecting and disconnecting said battery to said solenoid means in response to the pulse output of said timing pulse generator, said timing pulse generator causing said switching means to alternatively connect said solenoid means to said electrical power supply for a first prescribed short period of time of fixed duration so that said driving means is released and causes said expelling means to force fluid from said fluid chamber in said container means at a first prescribed rate greater than the selected prescribed average rate and to alternatively disconnect said solenoid means from said electrical power supply for a second prescribed short period of time so that the operation of said driving means is arrested by said stop clutch means to stop the fluid flow from said fluid chamber whereby the fluid is forced from said fluid chamber at the selected prescribed average rate over the sum of said first and second periods of time, said controller means further including adjustment means for selectively causing said timing pulse generator to vary the duration of only said second prescribed short period of time without varying the duration of said first prescribed period of time to selectively vary the selected prescribed average rate at which the fluid is forced from said fluid chamber into the patient.

6. The apparatus of claim 5 wherein said ratchet means includes a ratchet wheel rotatably driven by said driving means and defining a plurality of ratchet teeth around the periphery thereof; and a pivotally mounted stop dog operatively associated with said ratchet teeth to selectively arrest the rotation of said ratchet wheel, said solenoid means pivoting said stop dog to a release position releasing said ratchet teeth when said solenoid means is electrically actuated so that said driving means can operate, and pivoting said stop dog means to a check position when said solenoid means is electrically de-actuated so that said stop dog means engages said ratchet teeth to arrest the movement of said ratchet wheel to stop the operation of said driving means.

7. The apparatus of claim 6 wherein said driving means is a manually wound clockwork mechanism.

8. The apparatus of claim 6 wherein said first fixed period of time is shorter in duration than the length of time required for said driving means to move two adjacent ratchet teeth on said ratchet wheel past said stop dog.

9. Apparatus for selectively dispensing a fluid at a controlled slow rate into a patient comprising:
container means defining a fluid chamber therein for containing the fluid to be dispensed and defining a fluid outlet therefrom through which the fluid is to be dispensed into the patient;
a piston member slidably mounted in said fluid chamber for positively forcing the fluid from said fluid chamber as said piston member is moved toward the outlet end of said fluid chamber;
a drive screw operatively associated with said piston member and adapted to move said piston toward the outlet end of said fluid chamber as said drive screw is rotated in a first direction;
a spring driven clockwork mechanism including a drive spring and an output shaft rotatably driven at a controlled rate by said drive spring;
gearing means operatively connecting said output shaft on said clockwork mechanism with said drive screw so that said clockwork mechanism rotates said drive screw in said first direction;
a ratchet wheel operatively connected to said output shaft on said clockwork mechanism so that said output shaft rotates said ratchet wheel therewith, said ratchet wheel defining a plurality of ratchet teeth around the periphery thereof;
a pivotally mounted stop dog operatively associated with said ratchet teeth to selectively arrest the rotation of said ratchet wheel by engagement with said ratchet teeth;

an electrically operated solenoid connected to said sto dog for pivoting said stop dog to a release position out of engagement with said ratchet teeth when said solenoid is electrically actuated so that said clockwork mechanism can rotate the ratchet teeth thereby while rotating said drive screw and for pivoting said stop dog to a check position when said solenoid is electrically de-actuated so that rotation of said output shaft from said clockwork mechanism is arrested upon engagement of one of said ratchet teeth with said stop dog;

a battery;

a timing pulse generator powered by said battery and generating a timing pulse output; and switching means for alternately connecting said battery to said solenoid to electrically actuate said solenoid and disconnecting said battery from said solenoid to electrically de-actuate said solenoid, said switching means operatively connected to said timing pulse generator so that said switching means connects and disconnects said battery and said solenoid in response to said timing pulse output to control the average rate at which the fluid is forced from said fluid chamber into the patient.

10. The apparatus of claim 9 wherein said solenoid includes a return spring constantly urging said stop dog toward said check position so that said solenoid pivots said stop dog to said release position against the force of said return spring when said solenoid is actauted and said return spring pivots said stop dog to said check position when said solenoid is de-actuated.

11. The apparatus of claim 10 wherein said clockwork mechanism includes an escapement mechanism controlling the rotational speed of said output shaft.

12. The apparatus of claim 11 wherein said timing pulse output causes said switching means to actuate said solenoid for a period of time less than the length of time required for said clockwork mechanism to move two adjacent of said ratchet teeth past said stop dog each time said solenoid is actuated.

* * * * *